United States Patent [19]

Mizutani et al.

[11] Patent Number: 4,927,517
[45] Date of Patent: May 22, 1990

[54] NOX SENSOR HAVING CATALYST FOR DECOMPOSING NOX

[75] Inventors: Yoshihiko Mizutani, Nagoya; Hitoshi Nishizawa, Iwakura, both of Japan

[73] Assignee: NGK Insulators, Ltd., Japan

[21] Appl. No.: 343,682

[22] Filed: Apr. 27, 1989

[30] Foreign Application Priority Data

Apr. 30, 1988 [JP] Japan ................................ 63-108049

[51] Int. Cl.$^5$ ............................................. G01N 27/58
[52] U.S. Cl. ................................... 204/406; 204/410; 204/412; 204/425; 204/153.14
[58] Field of Search ............... 204/1 N, 410, 412, 425, 204/406; 338/34; 422/98

[56] References Cited

U.S. PATENT DOCUMENTS 4,770,760  9/1988  Noda et al. ........................ 204/425
4,772,376  9/1988  Yukawa et al. ..................... 204/410

FOREIGN PATENT DOCUMENTS 63-10781  3/1988  Japan .

Primary Examiner—G. L. Kaplan
Attorney, Agent, or Firm—Arnold, White & Durkee

[57] ABSTRACT

An NOx sensor having an electrochemical cell having a solid electrolyte body and a first and a second electrode, a portion that permits restricted communication of the first electrode with an external measurement gas space, a catalyst disposed adjacent the first electrode for decomposing NOx, a device for applying a current between the first and second electrodes, a current measuring device for detecting a current flowing between the first and second electrodes, an oxygen partial pressure measuring device for detecting an oxygen partial pressure of the atmosphere surrounding the first electrode, and a control device for calculating the concentration of NOx contained in the measurement gas in the external space, based on a first and a second current value. The current value is detected by the current measuring device when the oxygen partial pressure detected by the oxygen partial pressure measuring device is higher than a predetermined level above which the decomposition of NOx by the catalyst will not occur and below which the decomposition of NOx will occur. The second current value is detected when the oxygen partial pressure is lower than the predetermined level.

14 Claims, 6 Drawing Sheets

NOX SENSOR HAVING CATALYST FOR DECOMPOSING NOX

BACKGROUND OF THE INVENTION

1. Field of the Invention

The present invention relates generally to a device for determining the concentration of NOx (oxides of nitrogen) contained in a measurement gas, and more particularly to an NOx concentration sensor suitable for determining or measuring the concentration of Nox contained in exhaust gases or emissions produced by automotive internal combustion engines or various industrial furnaces, in order to control the combustion or burning condition of the engines or furnaces.

2. Discussion of the Prior Art

As a device for detecting or determining the oxygen concentration of gases, there is known an oxygen sensor which utilizes an oxygen-ion conductive solid electrolyte such as zirconia ceramics. An example of this type of oxygen sensor is disclosed in laid-open Publication No. 63-10781 (published March 9, 1988) of examined Japanese Patent Application. This oxygen sensor includes an electrochemical sensing cell and an electrochemical pumping cell each of which has an electrode exposed to an internal space which communicates, through suitable diffusion-resistance means, with the external space in which a gas to be measured (measurement gas) exists. The diffusion-resistance means provides a suitable diffusion resistance to the measurement gas. A controlled pumping current is applied to the pumpimg cell, based on the electromotive force induced by the sensing cell according to the principal of an oxygen concentration cell, so that the pumping cell operates to control the oxygen concentration of the atmosphere within the internal space to a predetermined level. The oxygen concentration of the measurement gas is determined by the pumping current when the oxygen concentration in the internal space is maintained at the predetermined level. Namely, the electromotive force $V_s$ induced by the sensing cell is compared with a reference voltage $V_r$, and the pumping current $I_p$ applied to the pumping cell is controlled in a feedback manner so that the electromotive force $V_s$ coincides with the reference voltage $V_r$.

SUMMARY OF THE INVENTION

It is an object of the present invention to provide an improved Nox sensor which includes at least one electrochemical cell having a first electrode exposed to an internal space into which a measurement gas diffuses from an external space through diffusion-resistance means under a predetermined diffusion resistance, the Nox sensor being operated based on a phenomenon experimentally recognized by the applicants, that the atmosphere adjacent the first electrode is not affected by the amount of Nox gases that will not be decomposed by a catalyst disposed close to the first electrode, when the oxygen partial pressure of the atmosphere adjacent the first electrode is higher than a predetermined level, while there arises a difference of the Nox concentration between the opposite ends of the diffusion-resistance means, due to the decomposition of the NOx gases by the catalyst, when the oxygen partial pressure adjacent the first electrode is lower than the predetermined level.

The above object may be achieved according to one aspect of the present invention, which provides an Nox sensor for determining the concentration of NOx contained in a measurement gas, comprising (a) an electrochemical cell having a solid electrolyte body, and at least two electrodes which are formed on the solid electrolyte body and which include a first electrode exposed to the measurement gas, and a second electrode, (b) diffusion-resistance means for restricted communication of the first electrode with an external space in which the measurement gas exists, the diffusion-resistance means having a predetermined resistance to diffusion of the measurement gas therethrough from the external space toward the first electrode, (c) a catalyst disposed adjacent the first electrode, for decomposing Nox contained in an atmosphere adjacent the catalyst, (d) current applying means for applying an electric current between the first and second electrodes of the electrochemical cell, (e) current measuring means for detecting an electric current flowing between the first and second electrodes, (f) oxygen partial pressure measuring means for detecting an oxygen partial pressure of the atmosphere surrounding the first electrode, and (g) control means for calculating the concentration of NOx contained in the measurement gas, based on a first current value and a second current value. The first current value is detected by the current measuring means when the oxygen partial pressure detected by the oxygen partial pressure measuring means is higher than a predetermined level above which the decomposition of Nox by the catalyst will not occur and below which the decomposition of Nox will occur. The second current value is detected by the current measuring means when the oxygen partial pressure detected by the oxygen partial pressure measuring means is lower than the predetermined level.

In one form of the above aspect of the invention, the NOx sensor further comprises a second electrochemical cell in addition to a first electrochemical cell which consists of the electrochemical cell having the first and second electrodes. The second electrochemical cell has a third electrode, which consists of the first electrode of the first electrochemical cell, and a fourth electrode exposed to a reference gas having a predetermined reference oxygen partial pressure. The third (first) and fourth electrodes are formed on the solid electrolyte body on which the first and second electrodes are formed. In this case, the oxygen partial pressure measuring means is constituted by the solid electrolyte body, the third (first) electrode, the fourth electrode, and voltage measuring means for detecting an electromotive force induced between the first and fourth electrodes.

In another form of the same aspect of the invention, the NOx sensor further comprises a second electrochemical cell in addition to a first electrochemical cell which consists of the electrchemical cell having the first and second electrodes. The second electrochemical cell has another solid electrolyte body, a third electrode exposed to a substantially same atmosphere as the atmosphere to which the first electrode is exposed, and a fourth electrode exposed to a reference gas having a predetermined reference oxygen partial pressure. In this case, the oxygen pressure measuring means is constituted by the second electrochemical cell, and voltage measuring means for detecting an electromotive force induced between the third and fourth electrodes.

In a further form of the same aspect of the invention, the oxygen partial pressure measuring means is constituted by the electrochemical cell having the first and second electrodes, and voltage measuring means for detecting an electromotive force induced between the first and second electrodes. The current applying means may be adapted to apply the electric current intermittently, so that the voltage measuring means may detect the electromotive force while the electric current is not applied between the first and second electrodes by the current applying means. the detected electromotive force is held for a predetermined time duration.

In a still further form of the same aspect of the invention, the oxygen partial pressure measuring means comprises a semiconductor oxide whose electrical resistance varies with the oxygen partial pressure of an atmosphere to which the semiconductor oxide is exposed, a pair of electrodes formed on the semiconductor oxide, and resistance measuring means connected between the pair of electrodes, for detecting the electrical resistance of the semiconductor oxide.

The first electrode may be formed of a material that enables the first electrode to function as the catalyst.

The object of the invention may also be achieved according to another aspect of the invention, which provides a NOx sensor for determining the concentration of NOx contained in a measurement gas, comprising a first and a second sensing unit, and control means. Each of the first and second sensing units comprises: (a) an electrochemical cell having a solid electrolyte body, and at least two electrodes which are formed on the solid electrolyte body which include a first electrode exposed to the measurement gas and a second electrode; (b) diffusion-resistance means for restricted communication of the first electrode with an external space in which the measurement gas exists, the diffusion-resistance means having a predetermined resistance to diffusion of the measurement gas therethrough from the external space toward the first electrode; (c) a catalyst disposed adjacent the first electrode, for decomposing NOx contained in an atmosphere adjacent the catalyst; (d) current applying means for applying an electric current between the first and second electrodes of the electrochemical cell; (e) current measuring means for detecting an electric current flowing between the first and second electrodes; and (f) oxygen partial pressure measuring means for detecting an oxygen partial pressure of the atmosphere surrounding the first electrode. The control means is adapted to calculate the concentration of NOx contained in the measurement gas, based on a first current value and a second current value. The first current value is detected by the current measuring means of the first sensing unit when the oxygen partial pressure detected by the oxygen partial pressure measuring means of the first sensing unit is higher than a predetermined level above which the decomposition of NOx by the catalyst of the first sensing unit will not occur and below which the decomposition of NOx will occur. The second current value is detected by the current measuring means of the second sensing unit when the oxygen partial pressure detected by the oxygen partial pressure measuring means of the second sensing unit is lower than a second predetermined level above which the decomposition of NOx by the catalyst of the second sensing unit will not occur and below which the decomposition of NOx will occur.

In one form of the above aspect of the invention, the control means controls the current applying means such that the oxygen partial pressure detected by the oxygen partial pressure measuring means of the first sensing unit is held at a level higher than the first predetermined level, while the oxygen partial pressure detected by the oxygen partial pressure measuring means of the second sensing unit is held at a level lower than the second predetermined level.

In the NOx sensor described above, the first electrode of the first sensing unit may be formed of a material that enables the first electrode to function as the catalyst.

The object of the invention may also be achieved according to a further aspect of the invention, which provides an NOx sensor for determining the concentration of NOx contained in a measurement gas, comprising a first and a second sensing unit, and control means. Each of the first and second sensing units comprises: (a) an electrochemical cell having a solid electrolyte body and at least two electrodes which are formed on the solid electrolyte body, which include a first electrode exposed to the measurement gas and a second electrode; (b) diffusion-resistance means for restricted communication of the first electrode with an external space in which the measurement gas exists, the diffusion-resistance means having a predetermined resistance to diffusion of the measurement gas therethrough from the external space toward the first electrode; (c) a catalyst disposed adjacent the first electrode, for decomposing NOx contained in an atmosphere adjacent the catalyst; (d) current applying means for applying an electric current between the first and second electrodes of the electrochemical cell; (e) current measuring means for detecting an electric current flowing between the first and second electrodes; and (f) oxygen partial pressure measuring means for detecting an oxygen partial pressure of the atmosphere surrounding the first electrode. The control means is adapted to calculate the concentration of NOx contained in the measurement gas, based on one of a first and a second combination of current values. The first combination consists of a first current value, a second current value and a third current value, while the second combination consists of the first and second current values, and a fourth current value. The first current value is detected by the current measuring means of the first sensing unit when the oxygen partial pressure detected by the oxygen partial pressure measuring means of the first sensing unit is higher than a first predetermined level above which the decomposition of NOx by the catalyst of the first sensing unit will not occur and below which the decomposition of NOx will occur, and the second current value being detected by the current measuring means of the first sensing unit when the oxygen partial pressure detected by the oxygen partial pressure measuring means of the first sensing unit is lower than the first predetermined level. The third current value is detected by the current measuring means of the second sensing unit when the oxygen partial pressure detected by the oxygen partial pressure measuring means of the second sensing unit is higher than a second predetermined level above which the decomposition of NOx by the catalyst of the second sensing unit will not occur and below which the decomposition of NOx will occur. The fourth current value is detected by the current measuring means of the second sensing unit when the oxygen partial pressure detected by the oxygen partial pressure measuring means of the second sensing unit is lower than the second predetermined level.

In one form of the above aspect of the invention, the control means is adapted to control the current applying means of the second sensing unit such that the oxygen partial pressure detected by the oxygen partial pressure measuring means of the second sensing unit is held at a level higher than the second predetermined level. In this case, the control means calculates the concentration of NOx based on the first combination of the first, second and third current values.

In another form of the above aspect of the invention, the control means is adapted to control the current applying means of the second sensing unit such that the oxygen partial pressure detected by the oxygen partial pressure measuring means of the second unit is held at a level lower than the second predetermined level. In this case, the control means calculates the concentration of NOx based on the second combination of the first, second and fourth current values.

In the Nox sensor described above, the first electrode of the first sensing unit may be formed of a material that enables the first electrode to function as the catalyst.

The object of the present invention may also be achieved according to a still further aspect of the invention, which provides an NOx sensor for determining the concentration of NOx contained in a measurement gas, comprising: a first and a second sensing unit, a catalyst provided in the first sensing unit, and control means. Each of the first and second sensing units includes: (a) an electrochemical cell having a solid electrolyte body and at least two electrodes which are formed on the solid electrolyte body, which include a first electrode exposed to the measurement gas and a second electrode; (b) diffusion-resistance means for restricted communication of the first electrode with an external space in which the measurement gas exists, the diffusion-resistance means having a predetermined resistance to diffusion of the measurement gas therethrough from the external space toward the first electrode; (c) current applying means for applying an electric current between the first and second electrodes of the electrochemical cell; (d) current measuring means for detecting an electric current flowing between the first and second electrodes; and (e) oxygen partial pressure measuring means for detecting an oxygen partial pressure of the atmosphere surrounding the first electrode. The catalyst is disposed adjacent the first electrode of the first sensing unit, for decomposing NOx contained in an atmosphere adjacent the catalyst. The control means is adapted to calculate the concentration of NOx contained in the measurement gas, based on a first current value and a second current value. The first current value is detected by the current measuring means of the first sensing unit when the oxygen partial pressure detected by the oxygen partial pressure measuring means of the first sensing unit is lower than a predetermined level below which the decomposition of NOx by the catalyst of the first sensing unit will occur and above which the decomposition of NOx will not occur. The second current value is detected by the current measuring means of the second sensing unit when the oxygen partial pressure detected by the oxygen partial pressure measuring means of the second sensing unit is at a predetermined value.

In the NOx sensor described above, the control means may be adapted to control the current applying means such that the oxygen partial pressure detected by the oxygen partial pressure measuring means of the second sensing unit is substantially equal to the oxygen partial pressure detected by the oxygen partial pressure measuring means of the first sensing unit.

In the NOx sensor according to the invention, an electrochemical cell operates to effect an electrochemical oxygen pumping operation with a controlled pumping current applied by the current applying means between the first and second electrodes, so that the atmosphere adjacent or surrounding the first electrode is controlled. The solid electrolyte body of this electrochemical cell may consist of an oxygen-ion conductive solid electrolyte material such as zirconia ceramic or a solid solution of $Bi_2O_3$ and $Y_2O_3$, or consist of a proton-conductive material such as $CrCe_{0.95} Yb_{0.05} O_{3-a}$.

The diffusion-resistance means functions to restrict a rate of diffusion of the meaurement gas from the external space into the internal space, providing a resistance to the diffusion of the measurement gas. The diffusion-resistance means may be provided by a pin hole with a small diameter which communicates with the internal space, a flat space with a small thickness which is provided as the internal space in communication with the external space, or a porous ceramic body which communicates with the external space and the internal space. For enhanced accuracy of measurement of the NOx concentration, it is desirable that the gradient of the oxygen concentration over the surface of the first electrode be as small as possible. To this end, it is preferable that the sensor has an internal space to which the first electrode is exposed, and suitable diffusion-resistance means for restricted communication between the external measurement gas space and the internal space.

The oxygen partial pressure measuring means may be constitutued by an electrochemical cell which consists of a solid electrolyte body and a pair of electrodes formed on the solid electrolyte body, and which produces an electromotive force according to the principle of an oxygen concentration cell. Alternatively, the oxygen partial pressure measuring means may be constituted by an arrangement which consists of a semiconductor oxide whose electrical resistance varies with the oxygen partial pressure of the atmosphere to which the semiconductor oxide is exposed, and a pair of electrodes formed on the semiconductor oxide. Where an electrochemical cell is used, this cell may partially or entirely function as an electrochemical pumping cell. In this case, a pumping current is applied to the pumping cell, intermittently or for predetermined time intervals, so that an electromotive force induced by the cell is measured to detect the oxygen partial pressure of the atmosphere surrounding the first electrode while the pumping current is not applied to the cell. This arrangement is desirable for avoiding an adverse influence of resistance polarization due to the pumping current, and thereby improving the accuracy of measurement.

The decomposition of NOx by the catalyst will not occur at the oxygen partial pressure of $10^{-2}-10^{-3}$ atm. or higher. This level of the oxygen partial pressure of the atmosphere surrounding the first electrode is almost equal to that of lean-burned exhaust gases emitted from automotive engines. Accordingly, the decomposition of NOx by the catalyst will occur at the oxygen partial pressure lower than the above-indicated level. However, the oxygen partial pressure used to permit the Nox decomposition is preferably higher than the level (e.g., $10^{-20}$ atm.) at which $CO_2$ and $H_2O$ begin to be reduced, so that the measurement of the NOx concentration is not influenced by the coexisting gases.

The catalyst used according to the present invention may be selected, for example, from among the platinum group metals such as PT, Rh and Pd, alloys of the platinum groups metals, and oxides of Cu, V, Cr, Fe, Ni, Co and Mn. The catalyst is positioned adjacent or close to the first electrode, so that the catalyst may communicate with the measurement gas which diffuses from the external space through the diffusion-resistance means, and decompose the NOx contained in the atmosphere surrounding the catalyst (i.e., the first electrode), when the oxygen partial pressure of the surrounding atmosphere is sufficiently lower than the level indicated above. The first electrode of the electrochemical cell may function as the catalyst, if the material of the first electrode is suitably selected.

BRIEF DESCRIPTION OF THE DRAWINGS

The foregoing and other objects, features and advantages of the present invention will become more apparent by reading the following description of presently preferred embodiments of the invention, when considered in connection with the accompanying drawings, in which.

DETAILED DESCRIPTION OF THE PREFERRED EMBODIMENTS

Figure 1:
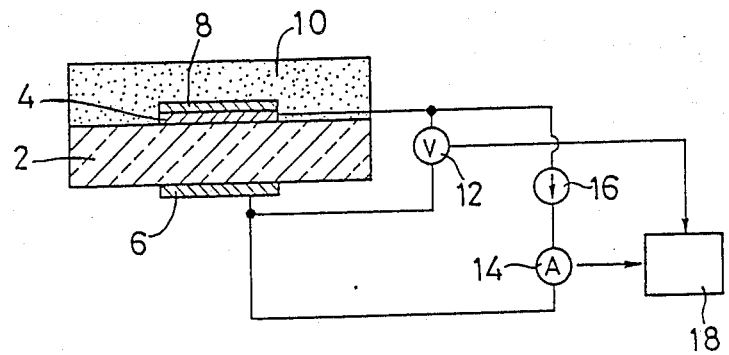
FIG. 1 is a schematic view partly in elevational cross section of an NOx sensor, for explaining the principle of the present invention.

According to the principle of the present invention, oxygen partial pressure measuring means is provided by an electrochemical cell which has a solid electrolyte body and a pair of electrodes formed on the solid electrolyte body. It is preferable that the NOx sensor according to the present invention employs one of the following three arrangements (a), (b) and (c), in connection with the oxygen partial pressure measuring means, for the reasons described below at (1), (2) and (3), respectively:

(a) The NOx sensor has a single electrochemical cell which serves not only as an oxygen pumping cell, but also as the oxygen partial pressure measuring means;

(b) The NOx sensor uses a common solid electrolyte body, and a first, a second and a third electrode formed on the common solid electrolyte body, such that the solid electrolyte body and hte first and second electrodes constitute a first electrochemical cell, while the solid electrolyte and the first and third electrodes constitute a second electrochemical cell which functions as the oxygen partial pressure measuring means; and (c) The NOx sensor uses a first electrochemical cell having a first and a second electrode, and a second electrochemical cell independent of the first electrochemical cell and having a third and a fourth electrode, the first anf third electrodes being exposed to substantially the same atmosphere. The second electrochemical cell functions as the oxygen partial pressure measuring means.

(1) The NOx sensor can be simplified in construction, and manufactured with a comparatively low cost;

(2) With the provision of the third electrode exposed to a reference gas having a reference oxygen partial pressure, the NOx sensor is capable of continuously determining the NOx concentration of the measurement gas, irrespective of whether the measurement gas is a rich-burned exhaust gas or a lean-burned exhaust gas;

(3) The oxygen partial pressure measuring means is not signifiantly affected by a pumping current applied to the first electrochemical cell, whereby the NOx sensor provides improved measuring accuracy.

For improved operating response to a change in the measurement gas, it is desirable to use two sensing units, first and second sensing units, rather than to use a single sensing unit wherein the atmosphere surrounding the first electrode is controlled so as to have a relatively high oxygen partial pressure or a relatively low oxygen partial pressure, as required to practice the principle of the present invention. Where the NOx sensor uses two sensing units, the oxygen partial pressure of the atmosphere surrounding the first electrode of the first sensing unit is controlled to be a relatively high level at which the decomposition of oxides of nitrogen (NOx) will not occur, while that of the second sensing unit is controlled to be a relatively low level at which the decomposition of NOx will occur. These two sensing units of the NOx sensor may be incorporated in separate respective housings, or alternatively in a single housing.

In the above case where the NOx sensor uses the two sensing units, the oxygen partial pressure of the atmosphere surrounding the first electrode of the first sensing unit may be made as low as that of the second sensing unit, for improved accuracy of measurement, where the first electrode of the first sensing unit is formed of Au, Au-Pt alloy or other materials which do not exhibit a catalytic function with respect to NOx.

For further improvement of the measuring accuracy of the NOx sensor with the two sensing units, it is desirable that the calculated value of the pumping currents of the two sensing units is normally kept at a reference value for determination of the NOx concentration, and the oxygen partial pressure surrounding the first electrode of the first sensing unit is lowered from time to time in order to measure the pumping current, so that the reference value indicated above is compensated based on the measaured pumping current. The relative values of the oxygen partial pressure of the first and second sensing units may be reversed to those indicated above.

Referring now to FIG. 1 which shows a basic arrangement embodying the principle of the present invention, reference numeral 2 denotes a planar solid electrolyte body which is made of an oxygen-ion conductive zirconia, for example, and reference numerals 4 and 6, respectively, denote a first and a second electrode which are formed on the opposite major surfaces of the solid electrolyte body 2. The two electrodes 4, 6 and the solid electrolyte body 2 cooperate with each other to constitute an electrochemical cell. Over the first electrode 4, there is formed a porous catalytic layer 8 for the decomposition of NOx. The first electrode 4 and the porous catalytic layer 8 are covered by a porous ceramic layer 10, which serves as diffusion-resistance means through which an external measurement gas diffuses under a certain diffusion resistance, toward the catalytic layer and first electrode 8, 4.

The electrochemical cell 2, 4, 6 is electrically connected to voltage measuring means 12, current measuring means 14, and current applying means 16. The voltage measuring means 12 detects an electromotive force induced between the first and second electrodes 4, 6 and the current measuring means 14 detects a current which flows between the electrodes 4, 6. The current applying means 16 is adapted to apply a current between the electrodes 4, 6. The outputs (detected electromotive force and current) of the voltage and current measuring means 12, 14 are received by control means 18, which determines the concentration of NOx contained in the measurement gas, based on the received inputs.

With the current applied from the current applying means 16 to the electrochemical cell 2, 4, 6, the cell operates as an oxygen pumping cell. Further, the electrochemical cell also functions as oxygen partial pressure measuring means (oxygen sensing cell) for determining the oxygen partial pressure of the measurement gas, based on an electromotive force induced to a difference in oxygen concentration between the atmospheres surrounding or adjacent the first and second electrodes 4, 6. The current measuring means 14 is adapted to detect a furst current value which is obtained when the oxygen partial pressure (determined by the electromotive force detected by the voltage measuring means 12) of the atmosphere surrounding the first electrode 4 is at a relatively high level at which the decomposition of NOx by the porous catalytic layer 8 will not occur. The current measuring means 14 also detects a second current value which is obtained when the oxygen partial pressure of the atmosphere surrounding the first electrode 4 is at a relatively low level at which the NOx decomposition by the catalytic layer will occur. The first and second current values are applied to the control means 18, so that the NOx concentration of the measurement gas is determined by the control means 18, based on the received first and second current values. As described later, the first and second current values have a given relationship relative to each other, with respect to the NOx concentration contained in the measurement gas.

Figure 2:
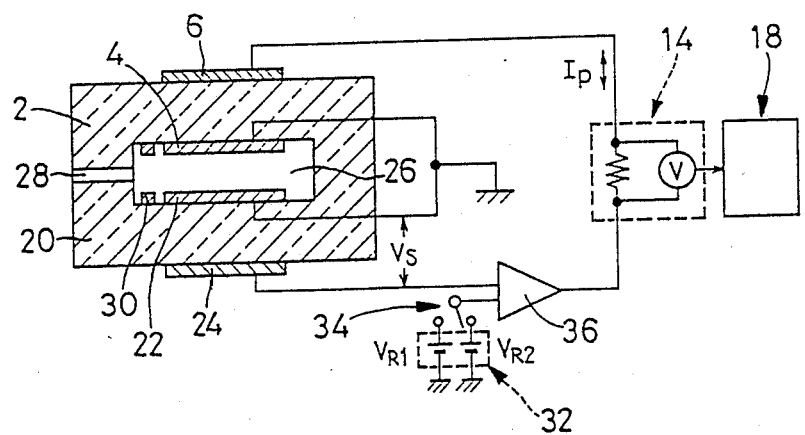
FIGS. 2, 3 and 4 are schematic views partly in elevational cross section showing different embodiments of the invention.

Referring next to FIG. 2, there is shown another embodiment of the NOx sensor of the present invention, wherein reference numeral 20 denotes a second solid electrolyte body which cooperates with the first solid electrolyte body 2 of the first electrochemical cell 2, 4, 6, to define an internal space 26, and diffusion-resistance means in the form of an orifice 28 which communicates with the internal space 26 and the external space in which the measurement gas exists. Reference numeral 30 designates a NOx decomposition catalyst, and reference numeral 32 designates a reference voltage power source which selectively provides two different reference voltages $V_{R1}$, $V_{R2}$, which are selected by a selector switch 34. The selected reference voltage is applied to an input of a comparator 36 which serves as current regulating means. The comparator 36 compares a received electromotive force between the third and fourth electrodes 22, 24, with the selected reference voltage of the reference voltage power source 32, and provides a pumping current $I_p$ so that the electromotive force is equal to the reference voltage. The pumping current $I_p$ is applied to the first electrochemical cell 2, 4, 6 so that the cell 2, 4, 6 operates to effect an oxygen pumping action so as to control the oxygen partial pressure (oxygen concentration) of the atmosphere within the internal space 26, to which the third electrode 22 is exposed. Thus, the comparator 36 serves as the means for regulating the oxygen pumping current $I_p$.

In the NOx sensor of FIG. 2, constructed as described above, the second electrochemical cell 20, 22, 24 functions as oxygen partial pressure measuring means for measuring the oxygen partial pressure within the internal space 26, depending upon the electromotive force between the third and fourth electrodes 22, 24. The electromotive force is compared alternately with the first reference voltage $V_{R1}$ (e.g., 80 mV) and the second reference voltage $V_{R2}$ (e.g., 500 mV). The pumping current values $I_{p1}$ and $I_{p2}$, established by the current regulating means 36 while the first and second reference voltages $V_{R1}$ and $V_{R2}$ are selected, are detected by the current measuring means 14, as the first and second current values, respectively. The control means 18 provides an output signal indicative of the NOx concentration of the measurement gas, which corresponds to a difference between the first and second current values. The fourth electrode 24 of the second electrochemical cell 20, 22, 24 is exposed to the measurment gas as a reference gas, and the instant NOx sensor is used primarily for determining the concentration of NOx in a lean-burned exhaust gas which includes residual oxygen, that is, the concentration of NOx contained in an exhaust gas which is produced as a result of combustion of a fuel-lean air-fuel mixture.

Figure 3:
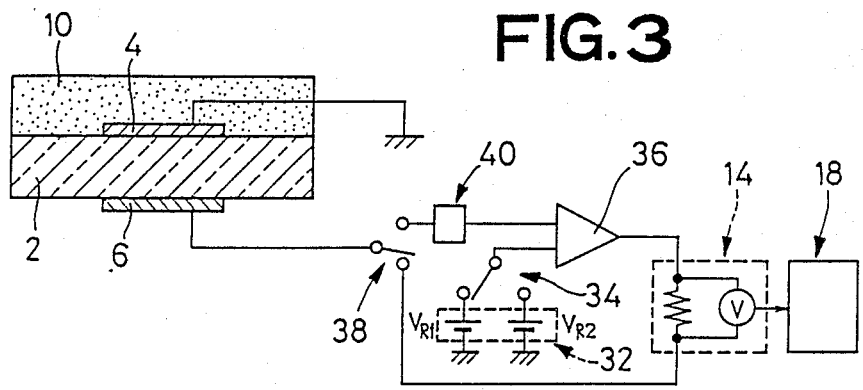

A further embodiment of the present invention is illustrated in FIG. 3, wherein the electrochemical cell 2, 4, 6 is operable alternately as an oxygen pumping cell and an oxygen sensing cell, depending upon the selected position of a selector switch 38. When the cell 2, 4, 6 is used as the oxygen sensing cell, values of the electromotive force between the first and second electrodes 4, 6 which represent the oxygen partial pressure of the atmosphere surrounding the first electrode 4 are sampled by and stored in a sample-and-hold means 40 for a predetermined time duration. In the present embodiment, the first electrode 4 is formed of a material which principally consists of a mixture of a platinum group metal such as Pt, Rh, and a ceramic such as zirconia. Thus, the first electrode 4 functions also as an NOx decomposition catalyst.

In operation of the NOx sensor of FIG. 3, the selector switch 38 is first placed in its position for operating the cell 2, 4, 6 as the oxygen sensing cell, namely, for connecting the second electrode 6 to the sample-and-hold means 40, in order to sample the electromotive force and store the sampled value in the sample-and-hold means 40. Then, the selector switch 38 is operated to connect the second electrode 6 to the current measuring means 14, so that the pumping current is applied to the cell, based on the sampled value stored in the sample-and-hold means 40. Described more specifically, the output of the sample-and-hold means 40 is compared with the selected first or second reference voltage $V_{R1}$, $V_{R2}$, and the outputs of the current regulating means 36 with the first and second reference voltages are used as the first and second current values, which are applied to the control means 18. The control means 18 produces an output signal indicative of a difference between the first and second current values, which is proportional to the NOx concentration of the measurement gas.

Examples

Figure 4:
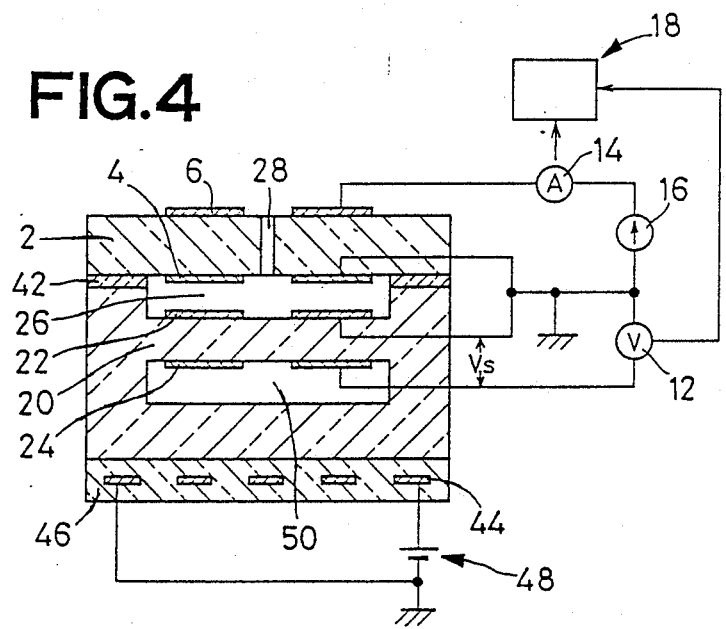
Figure 5A:
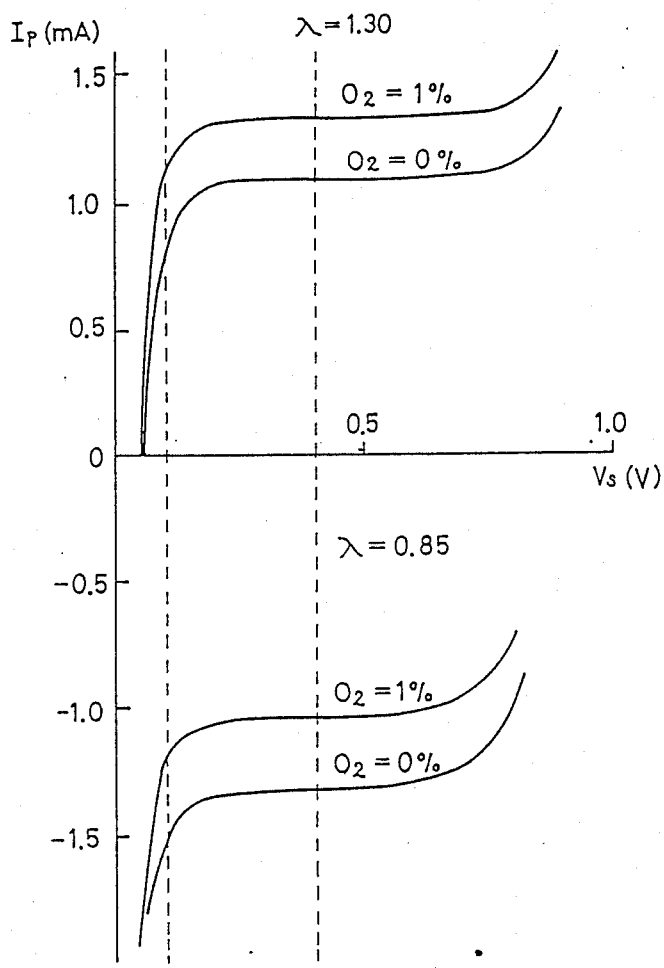
FIG. 5(a) is a graph indicating relationships betwen an oxygen partial pressure and a pumping current, which were obtained in the embodiment of FIG. 4, when oxygen gas was added and not added to measurement exhaust gases.
Figure 5B:
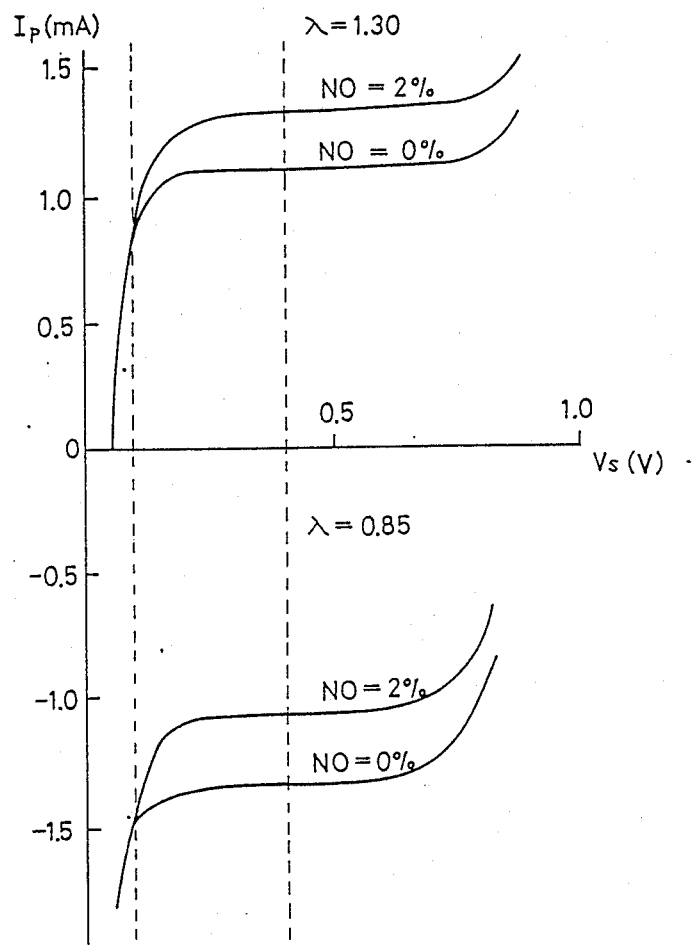
FIG. 5(b) is a graph indicating relationships similar to those of FIG. 5(a), which were obtained in the embodiment of FIG. 4, when NO gas was added and not added to the measurement exhaust gases.

An NOx sensor constructed according to an embodiment of the invention as shown in FIG. 4 was exposed to an exhaust gas produced as a result burning of propane. The pumping current $I_p$ and the electromotive force $V_s$ were measured. FIGS. 5(a) and 5(b) show the relationships between the measured pumping current and electromotive force.

In FIG. 4, reference numeral 42 designates an insulating layer which electrically insulates the first electrochemical cell 2, 4, 6 and the second electrochemical cell 20, 22, 24 from each other. To keep these two electrochemical cells at suitable operating temperatures, a heater 44 is embedded in a heater insulator (ceramic layer) 46 formed on the solid electrolyte body 20. The heater 44 is energized by a heater power source 48 so that the cells are heated to the suitable temperatures. Like the electrode 4 of the NOx sensor of FIG. 3, the first and third electrodes 4, 22 of this embodiment function also as an NOx decomposition catalyst. The fourth electrode 24 is disposed within an air passage 50, so that the electrode 24 is exposed to the ambient air introduced in the passage 50 as a reference gas. In the present specific example, the heater 44 was energized by a direct current of 12 V applied by the heater power source 48, so that the electrochemical cells were kept at about 800° C.

In FIG. 5(a), an uppermost curve indicated by $O_2=1\%$ represents a relationship between the pumping current $I_p$ and the electromotive force V, which were measured when 1% by volume of oxygen was added to the specimen propane gas which was produced as a result of burning of a propane-lean air-propane mixture whose excess air ratio λ is 1.30. A second curve from the top of the graph, indicated at $O_2=1\%$, represents the $I_p - V_s$ relationship when no oxygen was added to the lean-burned propane exhaust gas indicated above. Further, a third and a fourth curve in the graph represent the $I_p - V_s$ relationships corresponding to those of the first and second curves, when the specimen propane exhaust gases were produced as a result of burning of a propane-rich air-propane mixture whose excess air ratio λ is 0.85. It will be understood from the graph of FIG. 5(a) that the first and second curves associated with the lean-burned propane exhaust gases do not cross each other over substantially the entire range of the measured electromotive force $V_s$ (oxygen partial pressure of the atmosphere within the internal space 26 to which the first and third electrodes 4, 22 were exposed). In other words, the first and second curves have a substantially parallel relationship with each other, and represent a difference between the two pumping current values, which difference corresponds to the amount (1%) of the added oxygen. The third and fourth curves associated with the rich-burned propane exhaust gases have a similar relationship, to that of the first and second curves described above.

In FIG. 5(b), the upper two curves represent the $I_p - V_s$ relationships obtained when the NOx sensor was exposed to respective lean-burned propane exhaust gases (λ=1.30) to which 2% and 0% by volume of NO was added. The third and fourth curves represent the $I_p - V_s$ relationships obtained when the NOx sensor was exposed to respective rich-burned propane exhaust gases (λ=0.85) to which 2% and 0% by volume of NO was added. In this example, 2% of NO gas was added, since the amount of oxygen produced by decomposition of NO is one half (½) of the volume of NO gas. It will be understood from FIG. 5(b) that the first and second curves, and the third and fourth curves have substantially parallel relationships, when the oxygen partial pressure is lower than a given value (equivalent to an electromotive force $V_s$ equal to or higher than 100 mV). That is, a difference between the two current values represented by the first and second curves (or third and fourth curves) corresponds to the amount of the addition of NO, when the oxygen partial pressure is lower than the given value. Above this value (electromotive force $V_s$ being less than 100 mV), the two curves overlap each other, and the pumping currents obtained do not depend on the amount of NO contained in (added to) the specimen exhaust gases.

The above data indicates that the activity of the catalyst, i.e., the activity of the catalytic first and third electrodes 4, 22 made of a platinum group metal and zirconia in the embodiment of FIG. 4, is affected by the oxygen partial pressure of the atmosphere within the internal space 26 with which these electrodes 4, 22 communicate. Described more particularly, when the electromotive force $V_s$ is lower than 100 mV, the NO gas will not be decomposed by the catalysts (first and second electrodes 4, 22). However, when the electromotive force is equal to or higher than 100 mV, the NO gas will be decomposed by the catalysts, and the pumping currents have dependence upon the NO concentration.

Figure 6:
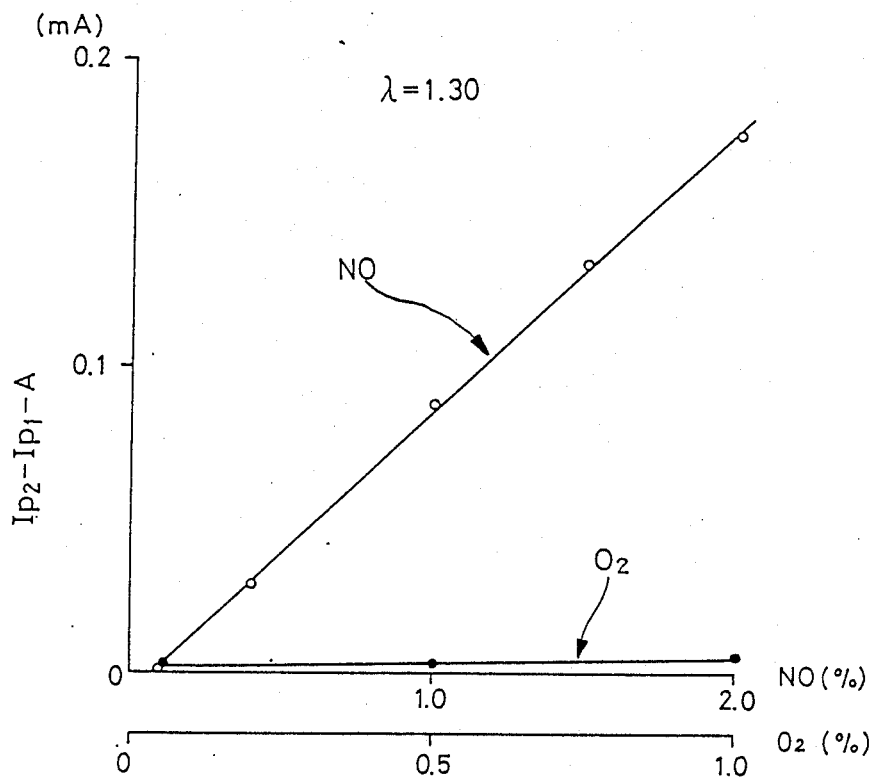
FIG. 6 is a graph showing the dependence of a sensor output obtained from the relationship curves of FIGS. 5(a) and 5(b), upon the amount of the oxygen gas and NO gas which were added to the measurement exhasut gases.

FIG. 6 shows relationships between a value ($I_{p2} - I_{p1} - A$), and the amounts of NO and $O_2$ added to the specimen exhaust gases. The first and second pumping currents $I_{p1}$ and $I_{p2}$ were measured when the electromotive force $V_s$ was 400 mV and 100 mV, respectively. The value "A" is a constant, compensating for a gradient in the amount of diffusion of oxygen within the internal space 26, due to a change in the distribution of pumping current in the electrode 4, which arises from a change in the oxygen partial pressure within the internal space 26. The value ($I_{p2} - I_{p1} - A$), calculated by the control means 18, is not substantially changed with the amount of oxygen ($O_2$) added, but is linearly changed with the amount of NO added. Thus, it was found that the NOx concentration of the measurement gas can be determined based on a difference between the second pumping current $I_{p2}$ obtained when the oxygen partial pressure within the internal space 26 is lower than the NOx decomposition level (below which NOx will not be decomposed), and the first pumping current $I_{p1}$ obtained when the oxygen partial presure in the space 26 is higher then the NOx decomposition level (above which NOx will be decomposed).

Figure 7:
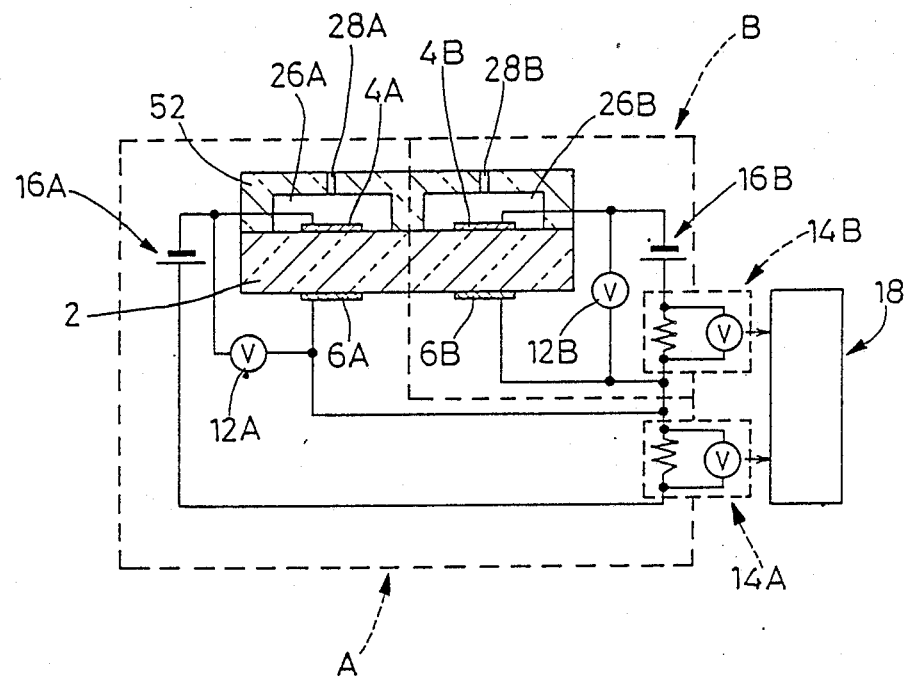
FIG. 7 is a schematic view corresponding to that of FIG. 2 illustrating a further embodiment of the present invention.

Referring next to FIG. 7, there is shown a further embodiment of the NOx sensor of the invention, which uses two sensing units, i.e., a first sensing unit A and a second sensing unit B, which are connected to the common control means 18. In the interest of brevity and simplification, the same reference numerals used in the preceding embodiments will be used to identify the corresponding components. However, reference characters A and B follow the reference numerals, to indicate whether the components belong to the first sensing unit A, or to the second sensing unit B. In the present embodiment, the oxygen partial pressures in the internal spaces 26A and 26B to which the first electrodes 4A and 4B are exposed are controlled to be substantially equal to each other, and the pumping currents $I_{pA}$ and $I_{pB}$ are measured in this condition. The control means 18 calculates a value $(I_{pA} - a \times I_{pB})$, and produces an output signal indicative of this value, which is proportional to the NOx concentration of the measurement gas. The value "a" is a constant, compensating for a variation in the diffusion resistances of the diffusion resistance means 28A and 28B of the first and second sensing units A, B. The first electrode 4A of the first sensing unit A is a thin film of Pt-Rh, while the first electrode 4B of the second sensing unit B is a thin film of gold. These two first electrodes 4A, 4B are formed by sputtering on the common solid electrolyte 2, and a dense ceramic body 52 is bonded to the solid electrolyte body 2 by a glass material. The first electrode 4A also serves as a catalyst. The first and second sensing units A and B use respective DC power sources 16A AND 16B, which apply a DC 0.7 V between the first and second electrodes 4A, 6A, and 4B and 6B, so that the oxygen partial pressures within the internal spaces 26A, 26B are compartively low.

While the present invention has been described in its preferred embodiment with a certain degree of particularity, it is to be understood that the invention is not limited to the details of the illustrated embodiments, but may be embodied with various changes, modifications and improvements which may occur to those skilled in the art without departing from the spirit and scope of the invention defined in the following claims.

What is claimed is:

1. An NOx sensor for determining the concentration of NOx contained in a measurement gas, comprising:
    an electrochemical cell having a solid electrolyte body, and at least two electrodes, formed on said solid electrolyte body, which includes a first electrode exposed to said measurement gas and a second electrode;
    diffusion-resistance means for restricted communication of said first electrode with an external space in which said measurement gas exists, said diffusion-resistance means having a predetermined resistance to diffusion of said measurement gas therethrough from said external space toward said first electrode;
    a catalyst disposed adjacent said first electrode, for decomposing NOx contained in an atmosphere adjacent said catalyst;
    current applying means for applying an electric current between said first and second electrodes of said electrochemical cell;
    current measuring means for detecting an electric current flowing between said first and second electrodes;
    oxygen partial pressure measuring means for detecting an oxygen partial pressure of the atmosphere adjacent said catalyst; and
    control means for calculating the concentration of NOx contained in said measurement gas, based on a first current value and a second current value, said first current value being detected by said current measuring means when said oxygen partial pressure detected by said oxygen partial pressure measuring means is higher than a predetermined level above which the decomposition of NOx by said catalyst will not occur and below which said decomposition of NOx will occur, and said second current value being detected by said curent measuring means when said oxygen partial pressure detected by said oxygen partial pressure measuring means is lower than said predetermined level.

2. The NOx sensor of claim 1, further comprising a second electrochemical cell in addition to a first electrochemical cell which consists of said electrochemical cell having said first and second electrodes, said second electrochemical cell having a third electrode, which consists of said first electrode of said first electrochemical cell, and a fourth electrode exposed to a reference gas of a predetermined reference oxygen partial pressure, said third and fourth electrodes being formed on said solid electrolyte body on which said first and second electrodes are formed, said oxygen partial pressure measuring means comprising said solid electrolyte body, said third electrode, said fourth electrode, and voltage measuring means for detecting an electromotive force induced between said first and fourth electrodes.

3. The NOx sensor of claim 1, further comprising a second electrochemical cell in addition to a first electrochemical cell which consists of said electrochemical cell having said first and second electrodes, said second electrochemical cell having another solid electrolyte body, a third electrode exposed to a substantially same atmosphere as the atmosphere adjacent said catalyst, and a fourth electrode exposed to a reference gas having a predetermined reference oxygen partial pressure, said oxygen partial pressure measuring means comprising said second electrochemical cell, and voltage measuring means for detecting an electromotive force induced between said third and fourth electrodes.

4. The NOx sensor of claim 1, wherein said oxygen partial pressure measuring means comprises said electrochemical cell and voltage measuring means for detecting an electromotive force induced between said first and second electrodes.

5. The NOx sensor of claim 4, wherein said current applying means applies said electric current intermittently, and said voltage measuring means detects said electromotive force while the electric current is not applied between said first and second electrodes by said current applying means, the detected electromotive force being held for a predetermined time duration.

6. The NOx sensor of claim 1, wherein said oxygen partial pressure measuring means comprises: a semiconductor oxide whose electrical resistance varies with the oxygen partial pressure of an atmosphere to which the semiconductor oxide is exposed; a pair of electrodes formed on said semiconductor oxide; and resistance measuring means connected between said pair of electrodes, for detecting the electrical resistance of said semiconductor oxide.

7. The NOx sensor of claim 1, wherein said catalyst is combined with said first electrode and said first electrode functions as said catalyst.

8. An NOx sensor for determining the concentration of NOx contained in a measurement gas, comprising:
    a first and a second sensing unit, each of which comprises: (a) an electrochemical cell having a solid electrolyte body and at least two electrodes, formed on said solid electrolyte body, which include a first electrode exposed to said measurement gas and a second electrode; (b) diffusion-resistance means for restricted communication of said first electrode with an external space in which said measurement gas exists, said diffusion-resistance means having a predetermined resistance to diffusion of said measurement gas therethrough from said external space toward said first electrode; (c) a catalyst disposed adjacent said first electrode, for decomposing NOx contained in an atmosphere adjacent the catalyst; (d) current applying means for applying an electric current between said first and second electrodes of said electrochemical cell; (e) current measuring means for detecting an electric current flowing between said first and second electrodes; and (f) oxygen partial pressure measuring means for detecting an oxygen partial pressure of the atmosphere adjacent the catalyst; and control means for calculating the concentration of NOx contained in said measurement gas, based on a first current value and a second current value, said first current value being detected by said current measuring means of said first sensing unit when said oxygen partial pressure detected by said oxygen partial pressure measuring means of said first sensing unit is higher than a first predetermined level above which the decomposition of NOx by said catalyst of said first sensing unit will not occur and below which said decomposition of NOx will occur, and said second current value being detected by said current measuring means of said second sensing unit when said oxygen partial pressure detected by said oxygen partial pressure measuring means of said second sensing unit is lower than a second predetermined level above which the decomposition of NOx by said catalyst of said second sensing unit will not occur and below which said decomposition of NOx will occur.

9. The NOx sensor of claim 8, wherein said control means controls said current applying means such that said oxygen partial pressure detected by said oxygen partial pressure measuring means of said first sensing unit is held at a level higher than said first predetermined level, while said oxygen partial pressure detected by said oxygen partial pressure measuring means of said second sensing unit is held at a level lower than said second predetermined level.

10. The NOx sensor of claim 8, wherein said catalyst is combined with said first electrode of said first sensing unit and said first electrode functions as said catalyst.

11. An NOx sensor for determining the concentration of NOx contained in a measurement gas, comprising:
a first and a second sensing unit, each of which comprises: (a) an electrochemical cell having a solid electrolyte body, and at least two electrodes formed on said solid electrolyte body which include a first electrode exposed to said measurement gas and a second electrode; (b) diffusion-resistance means for restricting communication of said first electrode with an external space in which said measurement gas exists, said diffusion-resistance means having a predetermined resistance to diffusion of said measurement gas therethrough from said external space toward said first electrode; (c) a catalyst disposed adjacent said first electrode, for decomposing NOx contained in an atmosphere adjacent the catalyst; (d) current applying means for applying an electric current between said first and second electrodes of said electrochemical cell; (e) current measuring means for detecting an electric current flowing between said first and second electrodes; and (f) oxygen partial pressure measuring means for detecting an oxygen partial pressure of the atmosphere adjacent the catalyst; and control means for calculating the concentration of NOx contained in said measurement gas, based on one of a first and a second combination of current values, said first combination consists of a first current value, a second current value and a third current value, while said second combination consists of said first and second current values, and a fourth current value, said first current value being detected by said current measuring means of said first sensing unit when said oxygen partial pressure detected by said oxygen partial pressure measuring means of said first sensing unit is higher than a first predetermined level above which the decomposition of NOx by said catalyst of said first sensing unit will not occur and below which said decomposition of NOx will occur, said second current value being detected by said current measuring means of said first sensing unit when said oxygen partial pressure detected by said oxygen partial pressure measuring means of said first sensing unit is lower than said first predetermined level, said third current value being detected by said current measuring means of said second sensing unit when said oxygen partial pressure measuring means of said second sensing unit is higher than a second predetermined level above which the decomposition of NOx by said catalyst of said sensing unit will not occur and below which said decomposition of NOx will occur, and said fourth current value being detected by said current measuring means of said second sensing unit when said oxygen partial pressure detected by said oxygen partial pressure measuring means of said second sensing unit is lower than said second predetermined level.

12. The NOx sensor of claim 11, wherein said control means controls said current applying means of said second sensing unit such that said oxygen partial pressure detected by said oxygen partial pressure measuring means of said second sensing unit is held at a level higher than said second predetermined level, said control means calculating the concentration of NOx based on said first combination of the first, second and third current values.

13. The NOx sensor of claim 11, wherein said control means controls said current applying means of said second sensing unit such that the oxygen partial pressure detected by said oxygen partial pressure measuring means of said second sensing unit is held at a level lower than said second predetermined level, said control means calculating the concentration of NOx based on said second combination of the first, second and fourth current values.

14. The NOx sensor of claim 11, wherein said catalyst is combined with said first electrode of said first sensing unit and said first electrode functions as said catalyst.

* * * * *